Figure 1:
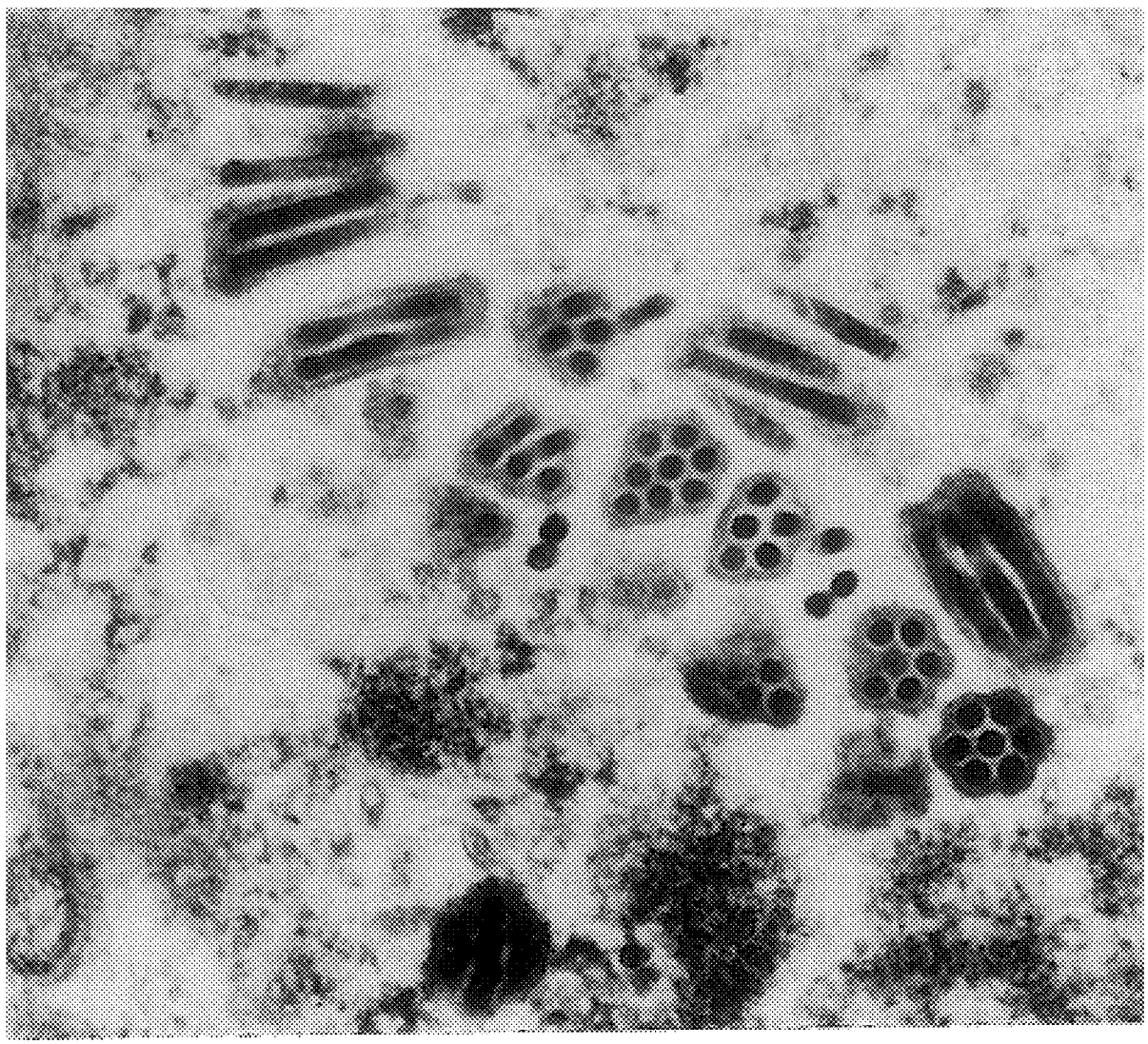

United States Patent [19]
Wood

[11] Patent Number: 6,090,379
[45] Date of Patent: *Jul. 18, 2000

[54] STABLE PRE-OCCLUDED VIRUS PARTICLE FOR USE IN RECOMBINANT PROTEIN PRODUCTION AND PESTICIDES

[75] Inventor: H. Alan Wood, Ithaca, N.Y.

[73] Assignee: Boyce Thompson Institute for Plant Research, Inc., Ithaca, N.Y.

[*] Notice: This patent issued on a continued prosecution application filed under 37 CFR 1.53(d), and is subject to the twenty year patent term provisions of 35 U.S.C. 154(a)(2).

[21] Appl. No.: 09/046,293

[22] Filed: Mar. 23, 1998

Related U.S. Application Data

[63] Continuation of application No. 08/705,213, Aug. 29, 1996, abandoned, which is a continuation-in-part of application No. 08/295,925, Aug. 25, 1994, Pat. No. 5,593,669, which is a continuation-in-part of application No. 08/091,535, Jul. 14, 1993, abandoned, which is a continuation-in-part of application No. 07/875,691, Apr. 29, 1992, abandoned.

[51] Int. Cl.$^7$ .......................... A61K 48/00; C12P 21/00; C12P 21/02; A01N 63/00

[52] U.S. Cl. ..................... 424/93.2; 424/93.6; 435/69.1; 435/183

[58] Field of Search ................................ 435/69.1, 172.1, 435/172.3, 320.1, 235.1; 424/405, 93.2, 93.6

[56] References Cited

U.S. PATENT DOCUMENTS 5,071,748 12/1991 Miller ..................................... 435/69.1
5,080,807 1/1992 Carr et al. .............................. 210/772

FOREIGN PATENT DOCUMENTS

| 8800198 | 1/1988 | Netherlands . |
|---|---|---|
| WO 90/01556 | 2/1990 | WIPO . |
| WO 90/14428 | 11/1990 | WIPO . |
| WO 92/06181 | 4/1992 | WIPO . |
| WO 92/15195 | 9/1992 | WIPO . |
| WO 93/03144 | 2/1993 | WIPO . |
| WO 93/09238 | 5/1993 | WIPO . |

OTHER PUBLICATIONS

PCT/US/03542, Mount Sinai School of Music, In Vivo Infection of Live Insects With A Recombinant Baculovirus, Prio date: Aug. 5, 88, pp 12.

Pennock et al, Mol & Cell. Biol., Mar. 1984, p 399–406, Strong and Regulated Expression of *Escherichia Coli* B–Galactosidase in Insect Cells With A Baculovirus Vector.

Smith et al, Jor. of Virology, May 1983, p 584–593, Molecular Engineering of the Autographa California Nuclear Polyhedrosis Virus Genome: Deletion Mutations Within the Polyhedrin Gene.

Carbonell et al., Gene 73 (1988) 409–418, Synthesis of a Gene Coding for an Insect–Specific Scorpion Neurotoxin and Attempts to Express It Using Baculovirus Vectors.

Luckow, V., Monsanto Corp. Res, 1990, pp 1–35, Cloning and Expression of Heterologous Genes in Insect Cells With Baculovirus Vectors.

Hammock et al, Expression and Effects of the Junenile Hormone Sterase in a Baculovirus, Nature, vol. 344, Mar. 1990, p. 458–460.

Maeda, S., Biochem. & Biophys. Res. Commun, vol. 165, No.3 1989, p. 1177–1183, Increased Insecticidal Effect by a Recombinant Baculovirus Carrying A Synthetic Diuretic Hormone Gene.

Maeda et al., Virology 184, 777–780 (1991), Insecticidal Effects of an Insect–Specific Neurotoxin Expressed by a Recombinant Baculo.

O'Reilly, D. et al., 1989, A Baculovirus blocks insect molting by producing ecdysteroid UDP–glucosyl transferase, Science 245:1110–1112.

Tomalski, M. et al., 1991, Insect Paralysis by baculovirus–mediated expression of a mite neurotoxin gene, Nature 352:82–85.

Merryweather, A. et al., 1990, construction of genetically engineered baculovirus insecticides containing the *Bacillus thuringiensis* subsp. *kurstaki* HD–73 delta endotoxin, J.Gen. Virol. 71:1534–1544.

Stewart, L. et al, Construction of an improved baculovirus insecticide containing an insect–specific toxin gene, Nature, pp 352:85–88 Jul., 1991.

O'Reilly, D. et al., 1991, Improvement of a Baculovirus pesticide by deletion of the EGT gene, Biotechnology 9:1086–1089.

Wood, H.A. et al, 1991, Genetically engineered baculoviruses as agents for pest control, Ann. Rev. Microbiol. 45: 69–87).

Maeda, S. et al., 1985, Production of human alpha–interferon in silkworm using a baculovirus vector, Nature 315: 592–594.

Granados, R. et al., 1986, In vivo infection and replication of baculoviruses, The Biology of Baculoviruses, p. 90–108.

Bishop, D. et al., 1988, Field trials of genetically–engineered baculovirus insecticides, p. 143–178.

Hamblin, M. et al, 1990, Co–occlusion and persistence of a baculovirus mutant lacking the polyhedrin gene, Appl. & Environ. Microbiol 56:3057–3062.

(List continued on next page.)

*Primary Examiner*—David Guzo
*Attorney, Agent, or Firm*—Brown, Pinnisi & Michaels, P.C.

[57] ABSTRACT

A method of infecting insects is disclosed; the method utilizes a form of a baculovirus which is highly efficient at establishing infection and is normally destined to become occluded within the polyhedrin or granulin—Pre-occluded Virus (POV). Specifically, the POV as derived from a polyhedrin-minus or granulin-minus (lacking a functional polyhedrin or granulin gene) baculovirus is fed to insect larvae per os resulting in high infection rates. The stabilization and use of the POV form of polyhedrin-minus baculoviruses for recombinant protein production and as an insecticide is also disclosed.

3 Claims, 1 Drawing Sheet

OTHER PUBLICATIONS

Federici, B., 1986, The Biology of Baculoviruses, vol. 1, Ultrastructure of Baculoviruses, p. 61–88.

Van Beek, N. et al., 1987, Alkaline liberated baculoviruses particles retained their infectivity per os for neonate lepidopterous larvae, J. Invertebrate. Pathol. 50:339–340.

Hughes, P. et al, 1981, A synchronous peroral technique for bioassay insect viruses, J. Invert. Pathol. 37:154–159.

Hughes, P. et al., 1986, A modified droplet feeding method for rapid assay of *Bacillus thuringiensis* and baculoviruses in noctuid larvae, J. Invert. Pathol. 48: 187–192.

Determination by Fluorescence Spectroscopy of the Volume Ingested by Neonate Lepidopterouse Larvae, Notes, Jour. of Invertebrate Pathology, 48, 249–251 1986.

Wood, H.A., 1980, Isolation and replication of an occlusion body–deficient mutant of the *Autographa californica* polyhedrosis virus, Virol. 105:338–344.

Wood, H.A., 1977, An agar overlay plague assay method for *Autographa californica* nuclear polyhedrosis virus, J. Invert. Pathol. 29:304–307.

Eldridge, et al., Appl. & Enviro. Micro, May 1992, p 1583–1591.

Kawai, et al, Anim. Sci. Tech., (Jpn) 63 (4) : 349–357 (1992) Production of Porcine Growth Hormone in Silkworm, etc.

Van Beek, N. et al., 1986, Determination of the volume ingested by neonate lepidopterous larvae using the fluorescent dye sodium fluorescein, J. Invert. Pathol. 48:249–251.

O'Reilly, et al., Baculovirus Expression Vectors, A Laboratory Manual, W.H. Freeman and Company, NY.

O'Reilly et al., Insect Biochem, Molec. Biol. vol. 22, No. 4 pp 313–320, 1992.

Bonning, B. et al, Insect Biochem, Molec., Bio. vol. 22, No. 5 pp. 453–458, 1992.

Volkman et al., Jnl. of Invertebrate Pathology, 30: 102–103.

Lesnaw, J., Oral Inoculation of Larvae with Recombinant Baculovirus, Invitrogen Corp. Digest, Mar. 1993, vol. 6—Issue 2.

van den Heuvel, 1993,J.F.J.M et al, Jour. of Virol. Methods, 42, pp. 207–216, A simple and efficient procedure for the oral inoculation of Trichoplusia ni larvae with polyhedrin-–negative recombinant baculovirus.

van den Heuvel, J.F.J.M. et al, Phytopathology for Sep., issued Aug. 1992, Expression of Discrete Potyvirus Gene Products By A Non–occluded Recombinant Baculovirus Fed to Trichoplusia ni Larvae.

Doane, et al, The Gypsy Moth: Research Toward Integrated Pest Management, U.S. Dept of Agric, 1981, pp. 461–466.

Shieh, T., Industrial Production of Viral Pesticides, Advances in Virus Research, vol. 36, pp. 315–343.

LeBlanc et al, 1991, Effect of Desiccation, pH, Heat & Ultraviolet Irradiation on Viability of *Baculovirus penaei*, Jol. of Invertebrate Pathology, 57, 277–286.

Davis et al, 1971, The Stability of a Purified Granulosis Virus of the European Cabbageworm, *Pieris brasicae*, in Dry Deposits of Intact Capsules, Jour. of Invert. Path. 17: 227–233.

Momoyamka et al., 1989, Inactivation of Baculoviral mid-–gut Glandnecrosis BMN virus by UV Irradiation, Sunlight Exposure, Heating & Drying, Fish Pathol. 24(2) , 115–118.

Birnbaum, M.J. et al, An Apoptosis–Inhibiting Gene From a Nuclear Polyhedrosis Virus Encoding a Polypeptide With Cys/His Sequence Motifs, Jnl. of Virology, Apr. 1994, pp. 2521–2528.

Murphy, F.A. et al, Virus Taxonomy, Archives of Virology, Supplement 10, Baculoviridae, pp. 104–113.

Smith, G.E. et al, DNA Homology Among Subgroup A,B, and C Baculoviruses, Virology 123, 1982, pp. 393–406.

Jehle, J.A. et al, The Granulin Gene Region of Cryptophlebia Leucotreta Granulosis Virus: Sequence Analysis and Phylogenetic Considerations, Jnl. of General Virology (1994), 75, pp. 3667–3671.

Crook, N.E. et al, Studies on the Genome Organization of CpGV Abstract only (W41–7), 1995.

Wood, H.A. et al., Per Os Infectivity of Preoccluded Virions from Polyhedrin–Minus Recombinant Baculoviruses, Jor of Invertebrate Pathology, 1993, 62: 4 pages.

Crook, Norman E., et al., Genome Characterization and Genetic Engineering of *Cydia pomonella* Granulosis Virus, Sep. 1, 1996, Universidad de Cordoba.

Winstanley et al., J. Gen. Virol., vol. 74, pp. 1599–1609, 1993.

Hashimoto et al., J. Gen. Virol., vol. 77, pp. 555–563, 1996.

Tanada et al., "Atlas of Invertebrate Viruses", Ed. Adams and Bonami, CRC Press, 1991, pp. 250–251, 1991.

Winstanley, D., 1996, Recombinant granulovsis viruses for improved biocontrol, Annual Report 1995–96, Horticulture Research International, p52–53.

STABLE PRE-OCCLUDED VIRUS PARTICLE FOR USE IN RECOMBINANT PROTEIN PRODUCTION AND PESTICIDES

REFERENCE TO RELATED APPLICATIONS

This is a continuation of application Ser. No. 08/705,213 filed Aug. 29, 1996, now abandoned, which is a continuation-in-part patent application of a parent patent application Ser. No. 08/295,925, filed Aug. 25, 1994, now U.S. Pat. No. 5,593,669, which is a continuation-in-part patent application of a parent patent application Ser. No. 08/091,535, filed Jul. 14, 1993, now abandoned, which is a file wrapper continuation-in-part application of parent patent application Ser. No. 07/875,691, filed Apr. 29, 1992, now abandoned.

FIELD OF THE INVENTION

This invention relates to Pre-occluded baculovirus particles; particularly to Pre-occluded virus particles derived from baculoviruses which have been genetically altered such that they lack a functional polyhedrin or granulin gene, and to the use of said particles to infect insect larvae per os.

BACKGROUND OF THE INVENTION

It is generally recognized that there are two infectious forms of baculoviruses. Early in the replication cycle, baculoviruses produce nucleocapsids in the nucleus of a host cell which bud through the nuclear membrane into the cytoplasm and subsequently bud through the plasma membrane. These extracellular virus particles are referred to as budded virus or nonoccluded virus (NOV). The NOV are highly infectious to susceptible insect tissue culture cells. Insect larvae can be infected by injection of NOV into the hemocoel (circulatory system). However, NOV is generally recognized as non-infectious when administered per os (feeding) to larvae. Generally, only very low infections rates can be achieved with high concentrations of NOV using per os larval inoculations. Accordingly, the NOV have been used to infect larvae per os only in rare instances and in the absence of other alternatives.

Late in a baculovirus replication cycle, the nucleocapsids do not bud through the nuclear membrane, and they become membrane bound within the cell nucleus. At the same time baculovirus polyhedrin or granulin genes are transcribed and translated producing large amounts of protein which crystallize around the membrane-bound nucleocapsids present in the nucleus. These protein crystals containing virus particles have historically been referred to as granules with granulosis viruses and polyhedra with nuclear polyhedrosis viruses (both are types of baculoviruses). It is well known in the art that granulin and polyhedrin are functionally identical and are maintained in baculoviruses that are functional identical and have been termed differently due to historical precedent.

The granules and polyhedra of baculoviruses are used to efficiently infect susceptible host larvae through per os inoculations. The alkaline pH in the larval gut region results in dissolution of the crystalline protein surrounding the occluded virus (OV) particles. Following release from the crystal, the OV particles are able to efficiently infect larval gut cells. Although highly infectious per os, the OV particles are generally recognized as having an extremely low potential to initiate infections with tissue culture cells or by injection into the hemocoel of susceptible host larvae.

Accordingly, the baculovirus literature reflects the use of NOV as the form of inoculum to infect host larvae by hemocoelic injections or to infect insect tissue culture cells by addition to cell culture medium. And the polyhedra containing OV are used to infect susceptible host larvae by per os inoculations.

The construction of most baculovirus expression vector systems (BEV) has been based on replacement of the polyhedrin gene coding region with a foreign gene under the transcriptional control of the polyhedrin gene promoter (Pennock, G. D., Shoemaker, C., Miller, L. K. 1984, "Strong and regulated expression of *Escherichia coli* b-galactosidase in insect cells with a baculovirus vector", Mol. and Cell. Bio. 4:399406; and Smith, G. E., Summers, M. D. and Fraser, M. J. 1983, "Production of human beta interferon in insect cells infected with a baculovirus expression vector", Molecular and Cell. Biol. 3:2156–2165). To date, hundreds of foreign genes have been expressed in BEV [Luckow, V. A 1990, "Cloning and expression of heterologous genes in insect Cells with baculovirus vectors in Recombinant DNA Technology and Applications", (C. Ho, A. Prokop and R. Bajpai eds.) McGraw-Hill, New York]. While the goal of most researchers has been to produce a protein for further study research or as a commercial product, there has been an increased interest in exploiting the BEV to express foreign proteins which would improve the pesticidal properties of the recombinant baculoviruses (Carbonell, L. F., Hodge, M. R, Tomalski, M. D., Miller, M. K., 1988, "Synthesis of a gene coding for an insect-specific scorpion neurotoxin and attempts to express it using baculovirus vectors", Gene 73:409–418; Hammock, B. D., Bonning, B. C., Possee, R. D., Hanzlik, T. N., Maeda, S., 1990, "Expression and effects of the juvenile hormone esterase in a baculovirus vector", Nature 344:458–461; Maeda, S., 1989, "Increased insecticidal effect by a recombinant baculovirus carrying a synthetic hormone gene", Biochem. Biophys. Res. Comm. 165:1177–1183; Maeda, S., Volrath, S. L., Hanzlik, T. N., Harper, S. A., Majima, K., Maddox, D. W., Hammock, B. D. and Fowler, E., 1991, "Insecticidal effects of an insect-specific neurotoxin expressed by a recombinant baculovirus", Virol. 184:777–780; Merryweather, A. T., Weyer, J., Harris, M. P. G., Hirst, M, Booth, T., Possee, R. D., 1990, "Construction of genetically engineered baculovirus insecticides containing the *Bacillus thuringiensis* ssp. *kurstaki* HD-73 delta endotoxin", J.Gen. Virol. 71:1534–1544; O'Reilly, D. R., Miller, L. K., 1989, "A Baculovirus blocks insect molting by producing ecdysteroid UDP-glucosyl transferase", Science 245:1110–1112; Stewart, L. M. D., Hirst, M., Ferber, M. L., Merryweather, A. T., Cayley, P. J., and Possee, R. D., 1991, "Construction of an improved baculovirus insecticide containing an insect-specific toxin gene", Nature 352:85–88; Tomalski, M. D. and Miller, L. K., 1991, "Insect paralysis by baculovirus-mediated expression of a mite neurotoxin gene", Nature 352:82–85; and O'Reilly, D. R. and Miller, L. K., 1991, "Improvement of a baculovirus pesticide by deletion of the EGT gene", Biotechnology 9:1086–1089). Baculoviruses are natural pathogens of many agriculturally important insect pests and are among the most promising alternatives to synthetic chemical pesticides (Wood, H. A. and R. R Granados, 1991, "Genetically engineered baculoviruses as agents for pest control", Ann. Rev. Microbiol. 45:69–87).

In order to assess the pesticidal properties of BEV, insect host larvae must be inoculated at known virus dosages during a specified period of time and the time course of infection followed. Deletion of the polyhedrin gene from BEV and the resultant lack of polyhedra production (and, therefore, the resultant absence of OVs) has been problematic to performing larval bioassays because the naturally occurring NOV is not very infections per os. Additionally, it has been proposed to infect insect larvae with BEV to produce proteins of commercial interest (Maeda, S., Kawai, T., Obinata, M., Fujiwara, H., Horiuchi T., Seki, Y., Sato, Y., and Furusawa, M., 1985, "Production of human alpha-interferon in silkworm using a baculovirus vector", Nature 315:592–594). Currently as demonstrated in all the references listed above, the common method of infecting larvae with BEV containing pesticidal or other foreign genes but lacking a functional polyhedrin gene (polyhedrin-minus virus) is by hemocoelic injection of larvae with the NOV. Alternatively, diet contamination with NOV has been used to establish infections, but very large doses are required due to the poor infectivity of this form of the virus by the oral route [Granados, R. R. and Williams, K. A., 1986, "In vivo infection and replication of baculoviruses" in The Biology of Baculoviruses Vol. I, "Biological Properties and Molecular Biology" (R. R. Granados and B. A. Federici, eds.), CRC Press, Boca Raton, Fla.].

The emphasis in the art has been on meeting the need for a method to simply and efficiently infect host insect larvae with polyhedrin-minus BEV isolates using per os inoculation procedures. The development of such a method would provide an efficient and simple means to: a) evaluate the pesticidal properties of a polyhedrin-minus BEV expressing foreign pesticidal gene products, b) infect large numbers of host insect larvae with polyhedrin-minus BEV expressing foreign proteins of commercial value (thereby, providing an alternative to BEV protein production in insect tissue culture cells), and c) to use polyhedrin-minus BEV expressing foreign pesticidal gene products as pesticides under field conditions.

The production of commercial protein products in insect larvae following infection with a polyhedrin-minus BEV currently would require larval NOV injections, a costly and laborious process. The commercial pesticide application of a polyhedrin-minus BEV expressing pesticidal proteins has been considered not possible by those schooled in the art. Such a pesticidal product would be ideal in that the progeny NOV (no polyhedra formed) would not persist in the environment [Bishop, D. H. L., Entwistle, P. F., Cameron, I. R., Allen, C. J., Possee, R. D., 1988, "Field trials of genetically-engineered baculovirus insecticides", in The Release of Genetically-engineered Micro-organisms, (eds. M. Sussman, C. H. Collins, F. A. Skinner, D. E. Stewart-Tull), Academic Press, NY; Hamblin, M., van Beek, N. A. M., Hughes, P. R., and Wood, H. A., 1990 "Co-occlusion and persistence of a baculovirus mutant lacking the polyhedrin gene", Applied and Environ. Microbiol. 56:3057–3062]. Because of the teachings of the current art, skilled artisans have directed much of their energies at either co-occlusion of polyhedrin-minus BEV with wild type virions (see above Hamblin et al. 1990, Miller, U.S. Pat. No. 5,071,748, Issued Dec. 10, 1991, filed May 15, 1989, and ACS and Price, International Application Published Under The Patent Cooperation Treaty, International Publication Number WO 90/01556, International Publication Date Feb. 22, 1990, International Application Number PCT/US89/03542) or constructing BEV which express foreign genes and a polyhedrin gene (polyhedrin-plus). The use of a polyhedrin-plus BEV as a commercial pesticide raises serious questions regarding persistence and competition of an engineered virus in the environment, from both ecological and health-safety standpoints.

It has been known in the art that late in the replication cycle of occluded baculoviruses, nucleocapsids become enveloped in bundles within the nucleus prior to being occluded by polyhedrin or granulin protein [Federici, B. A. 1986, Ultrastructure of baculoviruses in "The Biology of Baculoviruses Vol. I, Biological Properties and Molecular Biology" (R. R. Granados and B. A. Federici, eds.), CRC Press, Boca Raton, Fla.]. These virions are equally infectious per os when fed in polyhedra or following alkaline release and purification from the polyhedrin protein (Van Beek, N. A. M., Derksen, A. C. G., Granados, R. R. and Hughes, P. R., 1987, "Alkaline liberated baculoviruses particles retained their infectivity per os for neonate lepidopterous larvae", J. Invertbr. Pathol. 50:339–340). However, prior to this invention it was not known that these membrane bound virus particles destined to be occluded [which we refer to as pre-occluded virus (POV) particles], but not occluded if it derives from a polyhedrin-minus virus, were infectious per os. Furthermore, it was assumed in the art that infectious POV did not develop during replication of a polyhedrin-minus baculovirus; the continual and exhausting efforts in the art directed towards constructing pesticidal BEV with a polyhedrin gene in order to evaluate the biological properties as well as performing infectivity assays of polyhedrin-minus BEV by NOV injections or diet surface contamination with high concentrations of NOV illustrates the assumption of the non-existence of an infectious POV during replication of a polyhedrin-minus baculovirus.

In the publication entitled *Co-Occlusion and Persistence of a Baculovirus Mutant Lacking the Polyhedrin Gene* (Applied and Environmental Microbiology, Vol. 56, No. 10, October 1990, p. 3057–3062), Hamblin et al theorized that the secondary inoculum contained two types of virus particles: ExtraCellular Virus (ECV) in the hemolyph and intracellular virions which would normally be occluded in polyhedra. They believed they existed because they made the assumption that the infectivity shown may not have been possible from the ECV form of the virus. However, no experiments were performed to determine whether the observed infectivity was a result of the ECV, the intracellular virions or some other explanation. Even though some infectivity was shown, the inoculum was unstable and lost infectivity very rapidly. They came to the conclusion that in the absence of formation of polyhedra, these intracellular virions would not serve as an efficient inoculum. This conclusion is positively stated before and after the discussion of the theorized intracellular virions such that the paper as a whole teaches non-occluded virus cannot serve efficiently as a pesticide inoculum in the field. Hamblin et al did not teach how to isolate a POV particle, how to use a POV particle or how to differentiate a POV particle from any other form of a virus. Most importantly, Hamblin et al did not teach how to stabilize a POV particle so that it was infectious for more than a day after harvest.

Stabilizing virus particles can be quite difficult. Stabilization techniques that work for one virus may be disastrous for another virus. While freezing or lyophilization (freeze drying) have been used successfully to stabilize virus preparations, these techniques often fail or significantly reduce infectivity. Most studies that report stabilization by lyophilization do not report any data on the loss of infectivity. For instance, it is only important with vaccine preparations to retain some infectivity, but a loss of relative infectivity is not important. However, for large scale production of a pesticide, any loss in infectivity is crucial because that much more product needs to be prepared to accomplish the same task.

LeBlanc & Overstreet reported that desiccation for 48 hours inactivated *Baculovirus penaei.* (see "Effect of Desiccation, pH, Heat & Ultraviolet Irradiation on Viability of *Baculovirus penaei*", Journal of Invertebrate Pathology 57, 277–286 (1991)) David et al. showed that dry deposits of the granulosis virus of *Pieris brassicae* lost a significant amount of activity in only 2 days at 20° C. (see "The Stability of a Purified Granulosis Virus of the European Cabbageworm, *Pieris brassicae,* in Dry Deposits of Intact Capsules", Journal of Invertebrate Pathology, 17, 228–233 (1971))

In some respects, POV particles are similar to non-occluded baculoviruses. Momoyamka showed that Baculoviral mid-gut Gland necrosis BMN vinis (non-occluded baculovirus) was inactivated within 1.5 hours after drying at about 30° C. (see "Inactivation of Baculoviral mid-gut Gland necrosis BMN virus by UV Irradiation, Sunlight Exposure, Heating & Drying", Fish Pathol. 24(2), 115–118, (1989))

SUMMARY OF THE INVENTION

The inventor of the subject invention shows in the subject application that the formation and accumulation of POV occurs during the replication of a polyhedrin-minus baculoviruses (FIG. 1), and that these POV can be stabilized and are infectious per os using the neonate droplet feeding method (Hughes, P. R., Wood, H. A., 1981, "A synchronous peroral technique for the bioassay insect viruses", J. Invert. Pathol. 37:154–159; and Hughes, P. R., Van Beek, N. A. M., Wood, H. A., 1986, "A modified droplet feeding method for rapid assay of *Bacillus thuringiensis* and baculoviruses in noctuid larvae", J. Invert. Pathol. 48:187–192). Thus, this invention represents a simple solution to a problem in a manner which is contrary to the teachings and expectations of the prior art.

A method of infecting insects is disclosed; the method utilizes a form of a baculovirus which is highly efficient at establishing infection and is normally destined to become occluded within the polyhedrin or granulin—Pre-occluded virus particles (POV). Specifically, the POV produced during replication of polyhedrin-minus (genetic alteration resulting in nonfunctional polyhedrin or granulin gene) baculovirus is highly infectious to insect larvae when administered per os. The discovery of a stable POV form of polyhedrin-minus baculoviruses was essential to our invention of the novel method of infecting insect larvae per os using the POV form of polyhedrin-minus baculovirus, and as such is also described and taught in the specifications.

As stated above, stabilizing the POV without losing infectivity is very important. The inventor was genuinely surprised to discover that freeze-drying had little effect on the infectivity of the POV produced in larvae. Therefore, a stable and highly infectious POV preparation is one of the many important discoveries of the present invention.

It is therefore an object of this invention to disclose a novel method of infecting insects per os with POV formed during the replication of polyhedrin-minus or granulin-minus baculoviruses.

It is another object of this invention to disclose a novel method of making POV derived from polyhedrin-minus or granulin-minus baculovirus during the course of replication in insect tissue.

It is yet another object of this invention to disclose a novel pesticide; wherein said POV derived from a polyhedrin-minus or granulin-minus baculovirus is the active agent of said pesticide.

Further objects of the invention will be set forth in the description which follows, and will become apparent to those skilled in the art upon examination of the specification or by practice of the invention.

BRIEF DESCRIPTION OF THE DRAWING

FIG. 1 is an electron micrograph of Sf-21 insect tissue culture cells at 30 hours post infection with a recombinant baculovirus (polyhedrin-minus Ac-E10 isolates of *Autographa californica* nuclear polyhedrosis virus) which lacks a functional polyhedrin gene; the cells contain large numbers of pre-occluded virus particles.

DESCRIPTION OF THE PREFERRED EMBODIMENT

The naturally occurring, polyhedrin positive virus (polyhedrin-plus) was the 1A clone of AcNPV (Wood, H. A., 1980, "Isolation and replication of an occlusion body-deficient mutant of the *Autographa californica* nuclear polyhedrosis virus", Virol. 105–338–344). The polyhedrin-minus strain (Ac-E10) is a deletion mutant of the 1A clone which lacks a functional polyhedrin gene (Hamblin, M., van Beek, N. A. M., Hughes, P. R, Wood, H. A., 1990, "Co-occlusion and persistence of a baculovirus mutant lacking the polyhedrin gene", Appl. and Environ. Microbio. 56:3057–3062). The b-galactosidase producing, polyhedrin-minus virus (E2-b-gal) was obtained from MicroGenesys (Meriden, Conn.). The E2-b-gal virus lacks a functional polyhedrin gene and expresses b-galactosidase under the transcriptional control of the polyhedrin gene promoter. *Spodoptera frugiperda* cells, IPLB-SF-21 (Sf-21) (Vaughn, J. L., Goodwin, R. H., Tompkins, G. J., McCawley. P., 1977, "The establishment of two cell lines from the insect *Spodoptera frugiperda* (Lepidoptera:Noctuiadae)", In vitro 13: 213–217), were cultured in modified TNMFH medium (Wood, H. A., 1980, "Isolation and replication of an occlusion body-deficient mutant of the *Autographa californica* nuclear polyhedrosis virus", Virol. 105–338–344). Tissue culture plaque assays to determine NOV (nonoccluded or budded virus) titers were performed according to Wood (Wood, H. A., 1977, "An agar overlay plaque assay method for *Autographa californica* nuclear polyhedrosis virus", J. Invert. Pathol. 29:304–307).

The POV were prepared by infecting $9\times10^6$ Sf-21 cells with the Ac-E10 (polyhedrin-minus) virus in 6-well multi-well plates ($1.5\times10^6$ ( cells/well) at a multiplicity of infection of 10 plaque forming units (pfu) per cell and incubating the infected cells for 30 hours. This time period post infection was selected because it is known that polyhedrin protein expression occurs prior to 16 hours post-infection, and occlusion of OV particles takes place prior to 24 hours post infection (page 305 of Wood, H. A., 1977, "An agar overlay plaque assay method for *Autographa californica* nuclear polyhedrosis virus", J. Invert. Pathol. 29:304–307). Given the knowledge that POV particles are formed in polyhedrin-minus baculovirus infected cells, it was therefore expected that large numbers of POV particles would accumulate in the nucleus by 30 hours post infection. Higher concentrations of POV per cell may be reached at later time periods post infection.

FIG. 1 is an electron micrograph of Sf-21 insect tissue culture cells at 30 hours post infection with a recombinant baculovirus (polyhedrin-minus Ac-E10 isolate of*Autographa californica* nuclear polyhedrosis virus) which lacks a functional polyhedrin gene; the Ac-E10 infected cells contain large numbers of pre-occluded virus particles within their nucleus. The electron micrograph clearly shows the accumulation of multiple nucleocapsids enveloped within a single membrane. These particles are identical in appearance to those found in the cell nucleus of cells infected with a polyhedrin-plus virus (wild type virus) (page 78, FIG. 6A and 6E in Federici, B. A 1986, Ultrastructure of baculoviruses in "The Biology of Baculoviruses Vol. I, Biological Properties and Molecular Biology" [R. R. Granados and B. A Federici, eds.], CRC Press, Boca Raton, Fla.) (The Figures and text of the Federici, 1986 article mentioned-above is herein incorporated by reference). Furthermore, it is known in the art that baculovirus NOV particles are constructed of single nucleocapsids bound within a membrane (page 78, FIG. 6F in Federici, B. A. 1986 as above) and not multiple nucleocapsids bound within a membrane. Therefore, the multiple nucleocapsids (the black circles and rods [circles are views along the axis of the nucleocapsids and rods are longitudinal views of the nucleocapsids]) bound within a membrane (the dark gray enveloping each bundle of black circles or rods) in FIG. 1 are clearly POV particles derived from a polyhedrin-minus baculovirus (Ac-E10).

The infected cell samples containing the POV were harvested by twice pelleting the cells and resuspending the samples in tissue culture medium. Following harvesting, the cell samples were subjected to sonication sufficient to disrupt teem without altering the infectivity of the POV. The samples were then serially diluted and fed per os to *Trichoplusia ni* (cabbage looper) neonate larvae in a neonate feeding assay (Hughes, P. R., Wood, H. A., 1981, "A synchronous peroral technique for the bioassay insect viruses", J. Invert. Pathol. 37:154–159; and Hughes, P. R., Van Beek, N. A. M., Wood, H. A, 1986, "A modified droplet feeding method for rapid assay of *Bacillus thuringiensis* and baculoviruses in noctuid larvae", J. Invert. Pathol. 48:187–192). The volume ingested by the neonate larvae was determined (Van Beek, N. A. M., and Hughes, P. R., 1986, "Determination of the volume ingested by neonate lepidopterous larvae using the fluorescent dye sodium fluorescein", J. Invert. Pathol. 48:249–251). Based on the volume ingested per larvae, it was determined that following ingestion of approximately 1 cell equivalent 93% (28/30) of the larvae became infected.

Neonate bioassays of tissue culture samples infected with either the 1A or Ac-E10 virus isolates required dilutions of $10^{-2}$ to $10^{-3}$ to obtain infection levels of less than 100%. The Ac-E10 virus samples always exhibited higher infection levels than the 1A virus samples.

Although the cells were washed prior to sonication, it was considered that the samples could contain significant amounts of budded NOV. To determine if budded NOV contributed to the observed infectivity, neonate bioassays and tissue culture plaque assays were performed with Ac-E10 cell samples. As illustrated in Table 1, the Ac-E10 samples at 0 days postharvest contained 17 million pfu per milliliter. Based on a mean ingestion volumes of 26.4 nl, the larval uptake was approximately 343 pfu of NOV. Larval bioassays were then performed using 1A NOV samples, harvested prior to cell lysis to reduce contamination with POV and polyhedra. When 75 larvae ingested inocula containing from 324 to 528 pfu of NOV, no larval infections occurred. Therefore, the 93% infection level obtained with Ac-E10 infected cell samples were concluded to be the result of per os infectious POV.

When equivalent titers of NOV samples (prepared such that no POV were in the samples) or lysates from mock infected cells were used to inoculate test larvae, no deaths occurred. Accordingly, the high titer of infectious virus in the lysate of Ac-E10 infected cells was the result of the POV and not the result of NOV. This is consistent with the known art that NOV are not very infectious per os. For example, $3 \times 10^{4-6}$ plaque forming units of NOV were used to infect *Trichoplusia ni* larvae per os (page 460, FIG. 4 in Hammock, B. D., Bonning, B. C., Possee, R. D., Hanzlik, T. N., Maeda, S., 1990, "Expression and effects of the juvenile hormone esterase in a baculovirus vector", Nature 344:458–461).

The method of infecting insect larvae per os with a form of a baculovirus which is highly efficient at establishing infection and is normally destined to become occluded within the polyhedrin or granulin, therefore, comprises the steps of: a. infecting an insect host, wherein said insect host are selected from a group consisting of insect larvae, insect pupae, and in vitro insect cells, with a baculoviruses lacking a functional polyhedrin or granulin gene (polyhedrin-minus baculoviruses [e.g. NOV and polyhedrin-minus POV]), b. waiting for the progeny Pre-occluded virus particles derived from said baculovirus to form in said insect host, c. disrupting said insect host cells, which are housing said Pre-occluded virus particles, and d. feeding said disrupted cells and Pre-occluded virus particles per os to insect larvae.

Tissue culture POV samples diluted in tissue culture medium were held at 4 degrees centigrade for 2–3 weeks and reassayed to determine the stability of the infectivity of POV. The infectivity of the POV samples remained unaltered. Following cell harvesting, washing and sonication of Ac-E10 (polyhedrin-minus AcNPV) infected tissue culture cells, the samples were held at 4 degrees centigrade for 2 weeks. The POV sample remained infectious based on neonate feeding bioassays (infection and death of 16 of 24 test larvae resulted); therefore, the infectivity of POV can be stabilized by processing such as freeze-drying. Processing may be before or after disruption of the cells.

As shown in Table 1, the infectivity of the POV samples prepared in tissue culture cells remained constant following storage at 4° C. for 2 weeks.

TABLE 1

Determination of Preoccluded Ac-E10 Virus Stability with Trichoplusia in Neonate Larval Bioassays

| Days post-harvest | Sample dilution | PFU per ml[a] | Mean Volume Ingested (nl) | Percentage mortality[b] |
|---|---|---|---|---|
| 0 | $10^{-2}$ | $1.7 \times 10^7$ | 26.4 ± 8.2 | 93.3 |
| 6 | $10^{-2}$ | ND | 16.2 ± 6.4 | 96.6 |
| 14 | $10^{-2}$ | ND | 17.4 ± 6.7 | 96.5 |

[a]NOV plaque-forming units in the POV cell-associated sample as determined by a tissue culture plaque assay (Wood, 1977).
[b]Minimum of 25 larvae per group.

Freeze drying is an excellent method for stabilizing the POV particles produced in larvae. Prior to the present invention, any POV particles produced in larvae quickly lost their infectivity (see Hamblin et al.). Therefore, the stabilization of the POV particles was a critical step towards developing a useful preparation of POV.

As discussed in the Background Section of this application, drying of virus particles can sometimes significantly reduce infectivity rather than stabilize infectivity. In fact when POV is prepared in cell culture, freeze drying significantly reduces its infectivity. When POV was prepared in cell culture the $LD_{50}$ of the fresh preparation was 0.0194 cell equivalents per larva, whereas the $LD_{50}$ of the same preparation after lyophilization was 0.0461 cell equivalents per larva. The lyophilized material lost about 60% of its infectivity during lyophilization. When the same test was run with POV prepared in insects there was no loss in infectivity after lyopilization. Specifically, the $LD_{50}$ of the fresh preparation was 0.56(±0.25)ng fresh weight of diseased larvae per larva and the $LD_{50}$ of the lyophilized preparation was 0.55(±0.23)ng fresh weight of diseased larvae per larva.

There is no difference between a POV particle prepared in cell culture and a POV prepared in a larva. However, freeze drying works to stabilize the infectivity of the POV preparation from larvae, while it significantly reduces the infectivity of the POV preparation from cell culture. Given the fact the POV reacts differently to lyophilization in different situations, it would be impossible to predict whether lyophilization would stabilize or destroy POV infectivity prior to the present invention.

Assays with Freshly Prepared POV from Tissue Culture Cells

Based on the mean ingestion volumes of 16.2 to 26.4 nl and the sample containing $6 \times 10^6$ cell equivalents per milliliter, the average inoculum per larva contained from 0.97 to 1.58 cell equivalents of virus. Accordingly, the amount of POV produced within a single tissue culture cell was sufficient to infect more than 93% of the test larvae. Previous studies have shown that ingestion of an average dose of more that 25 polyhedra per larva is required to 90% infection of T. ni neonate larvae with the 1A virus (Hughes et al., 1984). Following infection of Sf-21 cells with the 1A virus, McKenna and Granados (unpublished data) have determined that an average of 8.1 polyhedra are produced per cell. Therefore, the number of infection units of POV per Sf-21 tissue culture cell is comparable to the infectivity of polyhedra produced per cell.

The POV bioassay procedure was used to assess the effect of the polyhedrin gene deletion and replacement of the polyhedrin gene with the b-galactosidase gene on survival time of infected larvae. A relationship between dosage and survival time has been documented (Van Beek et al., 1988). Therefore, in order to ensure that the larvae were infected with an equivalent dose (i.e., a single infections unit), dilutions of POV samples were used which infected less that 30% of the larvae. Median survival times ($ST_{50}$) were determined by the ViStat time program (Boyce Thompson Institute, 1990) and the results are presented in Table 2.

TABLE 2

Comparison of Survival Time following Infection with Wild-Type and Recombinant Preoccluded Virus

| Virus | Percentage mortality[a] | $ST_{50}$ ± SE (hours) |
| --- | --- | --- |
| 1A[b] | 27 | 75.0 ± 2.6 |
| E-10[c] | 20 | 85.0 ± 2.0 |
| E2-b-gal[d] | 28 | 102.5 ± 2.0 |

[a]Sixty larvae per group.
[b]The 1A clone isolated from the wild-type isolate of AcMPNV (Wood, 1980).
[c]The AcMNPV with the polyhedrin gene removed (Hamblin et al., 1990).
[d]The AcMNPV with the polyhedrin gene replaced with the bacterial lac Z gene.

The $ST_{50}$ of larvae infected with poly-minus virus (Ac-E10) was approximately 10 hours longer than that of larvae infected with the wild-type, poly-plus virus (1A), indicating that removal of the polyhedrin gene reduced the pesticidal property of the virus. The increase in $ST_{50}$ in the absence of polyhedrin protein production may result from a reduced demand on the cellular synthetic machinery or a reduced physical disruption in the absence of polyhedra formation.

The $ST_{50}$ of larvae infected with the poly-minus, b-galactosidase-producing virus (2E-b-gal) was 17 hr longer than the poly-minus virus (Ac-E10) infected larvae. Clearly, the production and/or biological activity of b-galactosidase resulted in increased survival times beyond that elicited by the elimination of polyhedrin protein production. Further investigations are needed to elucidate the mechanisms and parameters by which the lack of polyhedrin protein production and expression of b-galactosidase influence larval survival time. This is the opposite effect that would be desired for a pesticidal protein. However, the above data clearly show that the use of POV is important in a bioassay for assessing potential pesticidal proteins.

Infectious POV can also be obtained from homogenates of larvae or pupae infected with Ac-E10 or other polyhedrin-minus BEV, however, following death of the larvae or pupae, the infectivity is lost unless the preparation is diluted. The loss of infectivity presumably is caused by protease activity in the insect homogenate. This problem is solved by harvesting the larvae or pupae before they die or liquefy. Harvesting prior to liquification is critical to obtaining stable inoculum produced from larvae or pupae, but liquification occurs soon after death so all of the larvae or pupae should be harvested once the first few die.

Following infection of insect larvae per os with POV from a polyhedrin-minus baculovirus, or infection of tissue culture cells with NOV from a polyhedrin-minus baculovirus or insect pupae with NOV from a polyhedrin-minus baculovirus, progeny NOV and POV particles are formed. If the infecting baculovirus contains an expressed foreign gene insert (BEV), in addition to NOV and POV, the foreign gene product is also produced. For example, when POV of polyhedrin-minus baculovirus maintaining a foreign gene infects insect larvae per os (or when NOV maintaining an insert infects insect pupae or insect tissue culture cells) the foreign protein is expressed. When the POV of a polyhedrin-minus baculovirus containing a gene coding for b-galactosidase (E2-b-gal recombinant virus) was fed to insect larvae (*Trichoplusia ni*) per os, b-galactosidase was produced (the POV was obtained and infected the insect larvae using the method of infecting insect larvae per os as taught above in the specifications). This expression of the inserted gene of baculoviruses during replication of baculoviruses in an insect host is well known in the art [Luckow, V. A. 1990, "Cloning and expression of heterologous genes in insect Cells with baculovirus vectors in Recombinant DNA Technology and Applications", (C. Ho, A. Prokop and R. Bajpai eds.) McGraw-Hill, New York, pages 1–25]. The expressed gene products include therapeutic/vaccine proteins such as human immunodeficiency virus (HIV, HTLV-III) envelope protein, influenza virus hemagglutin protein, canine parvovirus coat protein, a- and b-interferon and interleukin-2 as well as pesticidal gene products such as BeIt insectotoxin 1, juvenile hormone esterase, *Androctonus australis* insect neurotoxin, and *Pyemotes tritici* insect neurotoxin.

Production of Recombinant Protein in Insect Larvae

The pre-occluded virus particles taught by the present invention can be used produce recombinant protein in insect larvae. Usually the baculovirus expression system is used in cell culture because the NOV form of the virus is not infectious per os. Otherwise, insect larvae are injected with the NOV form of the virus. While cell cultures have improved, they are still expensive and relatively fragile to maintain.

U.S. Pat. No. 5,351,643 granted to Hughes, teaches a high density rearing system for larvae. The cost of raising larvae is believed to be significantly cheaper than maintaining cell cultures on a per cell basis. However, the tedium and expense of injecting individual larvae has made large scale production of protein in larvae, impractical. The present invention teaches an efficient way of inoculating the insect larvae for production of recombinant protein.

Specifically, stabilized, pre-occluded baculoviruses lacking a functional granulin or polyhedrin gene is selected. The baculoviruses maintain and express a foreign gene product. The baculoviruses are used as an inoculum to infect insect larvae. Once the infection spreads, the infected insect larvae are harvested to collect the recombinant protein.

POV Insecticides

The data clearly demonstrate the utility of using POV of polyhedrin-minus, recombinant baculoviruses as pesticides and for the production of gene products such as those just mentioned above. In commercial practice a gene coding for a product, which would increase the pesticidal action of the virus or be a desired protein product, could be inserted into a polyhedrin-minus baculovirus which would produce POV. Following the teachings of this invention polyhedrin-minus POV may then be used to inoculate per os large numbers of insect larvae simply and cost effectively and express the inserted gene. Furthermore, polyhedrin-minus POV is also safe environmentally, because such a POV will not be occluded, and therefore it will not persist in the environment after it has infected and killed its host. Therefore, in addition to the efficient use of POV from polyhedrin-minus baculoviruses in infecting insect larvae per os for expressing a gene insert, the POV also has the additional advantage of being an environmentally safe genetically engineered baculovirus pesticide.

The POV is also attractive as a pesticide because more infectious units are produced per larva than with wild-type, polyhedrin-plus baculovirus. Using bioassays with neonate larvae, it can be shown than ingestions of 3.9 polyhedra per larvae will lead to infection of 50% of the larvae—3.9 polyhedra per $LD_{50}$. Based on the number of polyhedra produced per larva, there are $4 \times 10^8$ $LD_{50}$ units of polyhedra produced in a single larvae. When POV are produced under identical conditions, each larvae contains approximately $8 \times 10^8$ $LD_{50}$ units—a 2 fold increase. If the larval tissues are lyophilized, there is a slight loss of POV infectivity such that the increase is 1.5 fold over the polyhedral samples. Accordingly, the POV technology provides for a reduction in cost per unit of insecticide.

In larger scale field uses, the simple application of dust from lyophilized material onto plants or rehydration and spray application delivers an infectious pesticide. The stabilization of POV is discussed above and is critical to an effective POV insecticide. Both the occluded form of the virus and POV will be unstable on leaf surfaces due to exposure to sunlight. It is common knowledge that DNA is damaged when exposed to the UV radiation in sunlight. The point is that the occlusion body does not protect the virus exposed to sunlight, but will protect the virus in the soil. Formulation materials are added to reduce inactivation and to stabilize infectivity long enough to achieve infection with either the occluded or POV form. These procedures are well known in the art. Typically, commercial applications of the total number of polyhedra or POV produced in 100 larvae will be used per acre of an agricultural row crop. A larval equivalent is the amount of POV or polyhedra produced in an average infected larva. In the soil the occluded virus will persist for decades, whereas the POV will lose its infectivity within a week, an important and desirable ecological consequence.

Using the occluded virus which has been genetically altered would be an extreme environmental concern because of its long term persistence in the environment. The present invention teaches the solution to the problem of obtaining high infectivity, with extremely low residual environmental impact because it does not persist in the environment.

The field efficacy of POV as an insecticide was tested. The test also compared the infectivity of *Autographa californica* nuclear polyhedrosis virus (AcMNPV) POV and polyhedra. The test site was a two acre site containing four replica plots for the application of each treatment (POV, polyhedra and a control).

The applications rate was about 30 gallons per acre and 100 larval equivalents of each treatment per 30 gallons. The field infectivity of the amount of POV and polyhedra were compared. The POV and polyhedra equivalents were mixed with typical sticker/spreaders in order to obtain good coverage of the plants. The insecticide formulation used was: 0.7 ml/liter of "BOND" sticker spreader, 1.9 ml/liter skim milk and inoculum (all diluted in water).

The cabbage plants were seeded with late third instar *Trichoplusia ni* larvae prior to the spray applications. At four or five days post spray, the larvae were harvested from each of the 4 replicas of the POV, polyhedra and control plots. The larvae were placed individually in cups containing rearing diet and incubated at 28° C. until death or pupation. Harvesting was done at 4 or 5 days because previous field tests with this virus and insect showed that it was the optimal time to harvest infected larvae because the infected larvae began dying after 5 days and would be lost from the test.

All dead larvae were examined to ensure that death had occurred from the virus inoculum. In other words, with dead larvae from the POV plots, it was verified that the larval tissues contained no polyhedra. With dead larvae from the polyhedra plots, it was verified that the tissues contained polyhedra and that they were the size of AcMPNV polyhedra. This is not a typical procedure with field testing of baculoviruses. It is important to make these observations to ensure that naturally occurring viruses do not alter the data. The results of the field release are shown in Table 3.

TABLE 3

Effects of Field Release of POV Compared to Wild Type Virus Polyhedra

| Virus Inoculum | Mean Percent Death Exp 1 | Mean Percent Death Exp 2a | Mean Percent Death Exp 2b |
| --- | --- | --- | --- |
| POV | 82% | 35% | 49% |
| Polyhedra | 76% | 91% | 96% |

Corrected for control mortality

The field release shows that POV is highly infectious under laboratory and field conditions. Also, the POV and polyhedra produced in the same amount of larval tissue exhibit comparable levels of infectivity under field conditions. Experiments 2a and 2b were successive 2 week experiments on the same field. The small differences in infectivity of the POV may be due to the fact that POV is more susceptible to environmental conditions. The formulation of POV insecticide can be improved. One aspect of the formulations that may be important is that the freeze dried larvae containing POV contain non water soluble materials such as fats whereas polyhedra readily suspend in water. It is possible that a more efficient POV insecticide could be achieved through emulsification of the preparation.

The achievement of a proven POV field insecticide is a great achievement in the art. POV is known to be very susceptible to environmental conditions and this is in fact its value. Many factors could have prevented its infectivity. The pH of dew and rain on the leaf surface has been shown to have an effect on infectivity of virus particles. The effect of prolonged exposure to UV radiation (i.e. sunlight), the heat, and repeat drying and rehydration cycles were all potentially a concern. Furthermore, prior to the field release, the infectivity of POV per os had only been tested on artificial media. The surface of a plant in the field is very different than the surface of artificial diet in a rearing cup. Plants produce many potentially harmful substances that could have affected the infectivity of POV. By the work disclosed herein, the applicant has shown for the first time that an insecticide including a POV can be achieved.

Soil samples were taken at the end of the growing season and infectivity assays conducted. Infectious polyhedra were isolated from the soil in the polyhedra plots. However, as expected based on the suicide nature of POV, no infectious POV was isolated from the POV plots.

Accordingly, it is to be understood that the embodiments of the invention herein described are merely illustrative of the application of the principles of the invention. Reference herein to details of the illustrated embodiments are not intended to limit the scope of the claims, which themselves recite those features regarded as essential to the invention.

I claim:

1. A method of producing recombinant protein, comprising:
    a. selecting stabilized, pre-occluded baculoviruses lacking a functional polyhedrin gene wherein said baculovirus maintains and expresses a foreign gene product but not a polyhedrin gene;
    b. using said stabilized, pre-occluded baculoviruses as an inoculum to infect insect larvae; and
    c. harvesting said infected insect larvae to collect said recombinant protein.

2. The method of claim 1, wherein said foreign gene codes for a pesticidal protein.

3. The method of claim 1, wherein said foreign gene codes for an enzyme or therapeutic protein.

* * * * *